United States Patent [19]
Chou

[11] Patent Number: 6,151,968
[45] Date of Patent: Nov. 28, 2000

[54] WRIST BAND TYPE ELECTRONIC SPHYGMOMANOMETER

[76] Inventor: Deng-Jeng Chou, No. 21. Chung Msiao E. Rd., Sec. 2., Taipei City, Taiwan

[21] Appl. No.: 09/008,298

[22] Filed: Jan. 16, 1998

[51] Int. Cl.[7] ........................................... G01L 7/20
[52] U.S. Cl. ..................... 73/748; 128/672; 128/690; 128/2.05 T
[58] Field of Search .................. 73/748; D10/31; 128/672, 690, 2.05

[56] References Cited

U.S. PATENT DOCUMENTS

| | | | |
|---|---|---|---|
| D. 355,858 | 2/1995 | Sugita | D10/31 |
| 4,129,124 | 12/1978 | Thalmann | 128/2.05 |
| 4,409,983 | 10/1983 | Albert | 128/690 |
| 5,485,848 | 1/1996 | Jackson et al. | 128/672 |
| 5,615,179 | 3/1997 | Yamamoto et al. | 368/281 |

*Primary Examiner*—Harshad Patel
*Assistant Examiner*—Jewel V. Thompson
*Attorney, Agent, or Firm*—Rosenberg, Klein & Lee

[57] ABSTRACT

A wrist band type electronic sphygmomanometer including an inflatable wrist band for fastening to the user's wrist, a rubber-bulb operated to inflate the inflatable wrist band, a relief valve controlled to release air from the inflatable wrist band, and an electronic manometer and timepiece assembly provided at the wrist band to indicate time and to measure and indicate the user's blood pressure and strength of pulse beat through a pressure sensor thereof.

1 Claim, 3 Drawing Sheets

WRIST BAND TYPE ELECTRONIC SPHYGMOMANOMETER

BACKGROUND OF THE INVENTION

The present invention relates to a sphygmomanometer, and more particularly to a wrist band type electronic sphygmomanometer which is a combination of a blood pressure manometer, a pulse-meter and an electronic watch.

A regular mechanical sphygmomanometer is comprised of a rubber-bulb (blower), a cuff, and a mercury manometer. This structure of mechanical sphygmomanometer is heavy and not convenient for carrying with the user, and commonly used in hospitals. Recently, a variety of electronic sphygmomanometers have been developed for home use. However, these electronic sphygmomanometers consume much battery energy. Further, these electronic sphygmomanometers are not convenient for use as one's personal item.

SUMMARY OF THE INVENTION

It is one object of the present invention to provide an electronic sphygmomanometer which is designed to measure time and the user's blood pressure and strength of pulse beat. It is another object of the present invention to provide an electronic sphygmomanometer which is designed to be carried on one's wrist for personal use. It is another object of the present invention to provide a wrist band type electronic sphygmomanometer which is inexpensive. According to the present invention, the electronic sphygmomanometer comprises an inflatable wrist band for fastening to the user's wrist, a rubber-bulb operated to inflate the inflatable wrist band, a relief valve controlled to release air from the inflatable wrist band, and an electronic manometer and timepiece assembly provided at the wrist band to indicate time and to measure and indicate the user's blood pressure and strength of pulse beat through a pressure sensor thereof.

DETAILED DESCRIPTION OF THE PREFERRED EMBODIMENT

Figure 1:
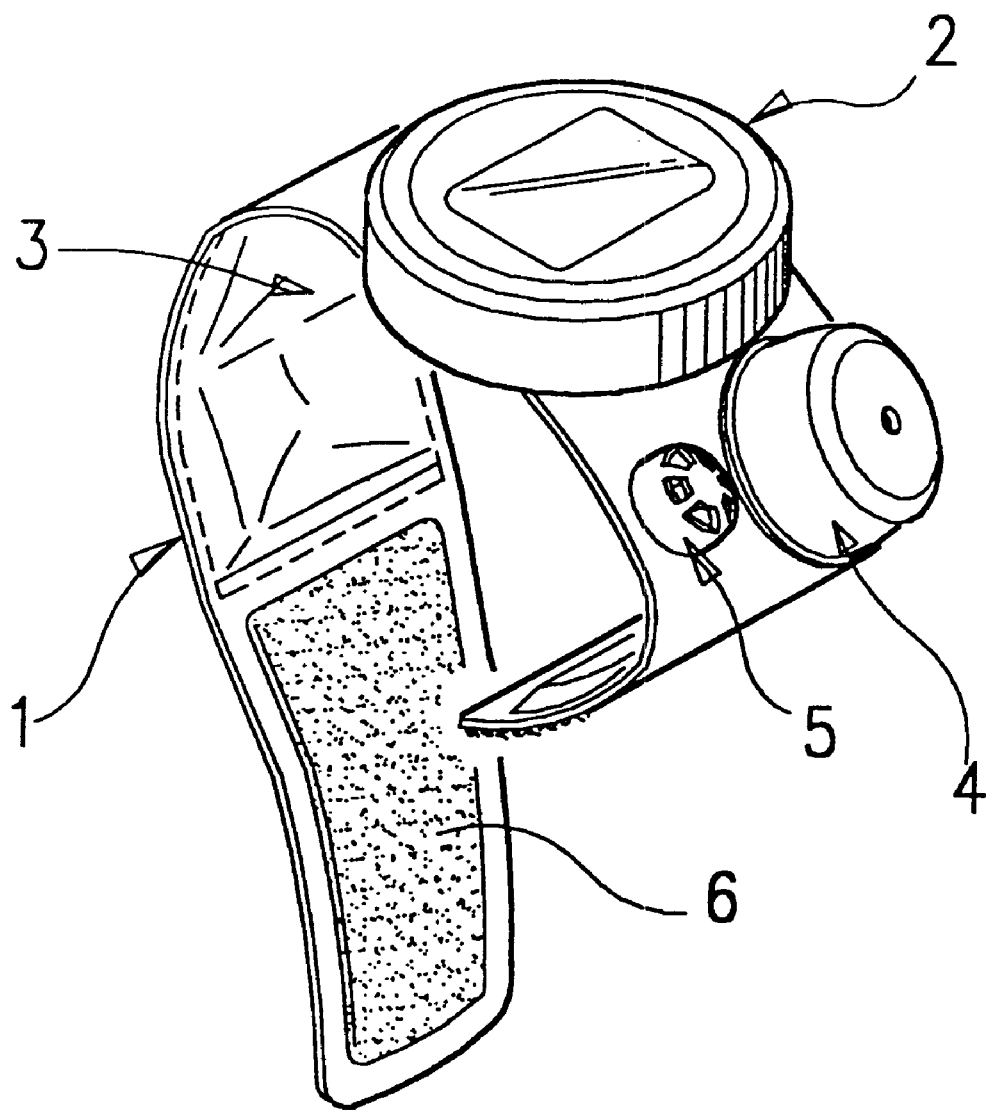
FIG. 1 is a perspective view of a wrist band type electronic sphygmomanometer according to the present invention.

Referring to FIG. 1, a wrist band type electronic sphygmomanometer in accordance with the present invention comprises a wrist band 1. The wrist band 1 comprises an inflatable chamber longitudinally extended to its both ends. Hook and loop materials 6 are provided for joining both ends of the wrist band 1. An electronic manometer and timepiece assembly 2 is provided at the wrist band 1 on the middle for measuring and indicating the pressure of the blood, the strength of the pulse beat, and time. A rubber-bulb 4 is provided at the wrist band 1, and operated to inflate the inflatable chamber 3. A relief valve 5 is provided at the wrist band 1, and operated to release air from the inflatable chamber 3.

Figure 2:
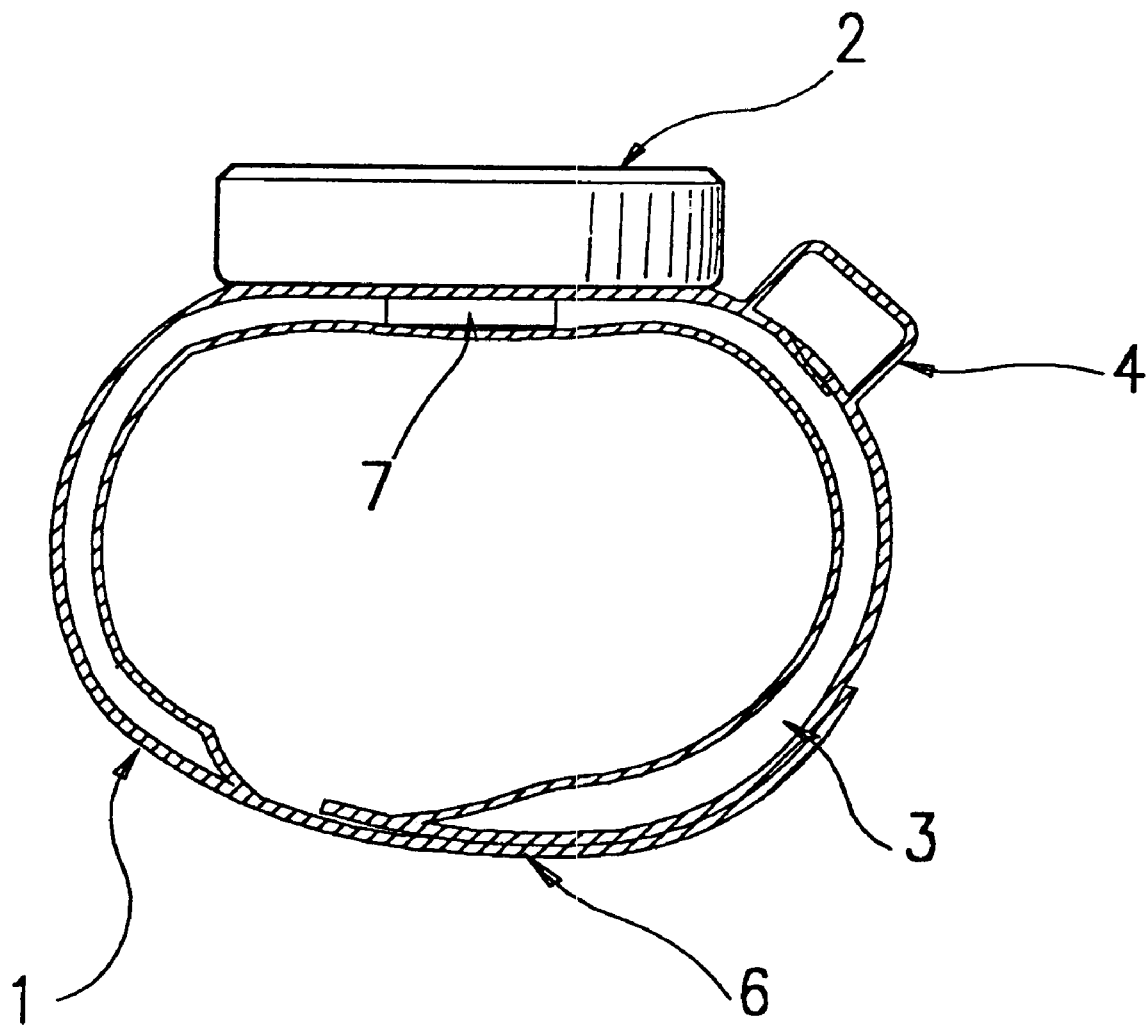
FIG. 2 is a sectional view of the wrist band type electronic sphygmomanometer of the present invention, showing the inflatable chamber inflated.
Figure 3:
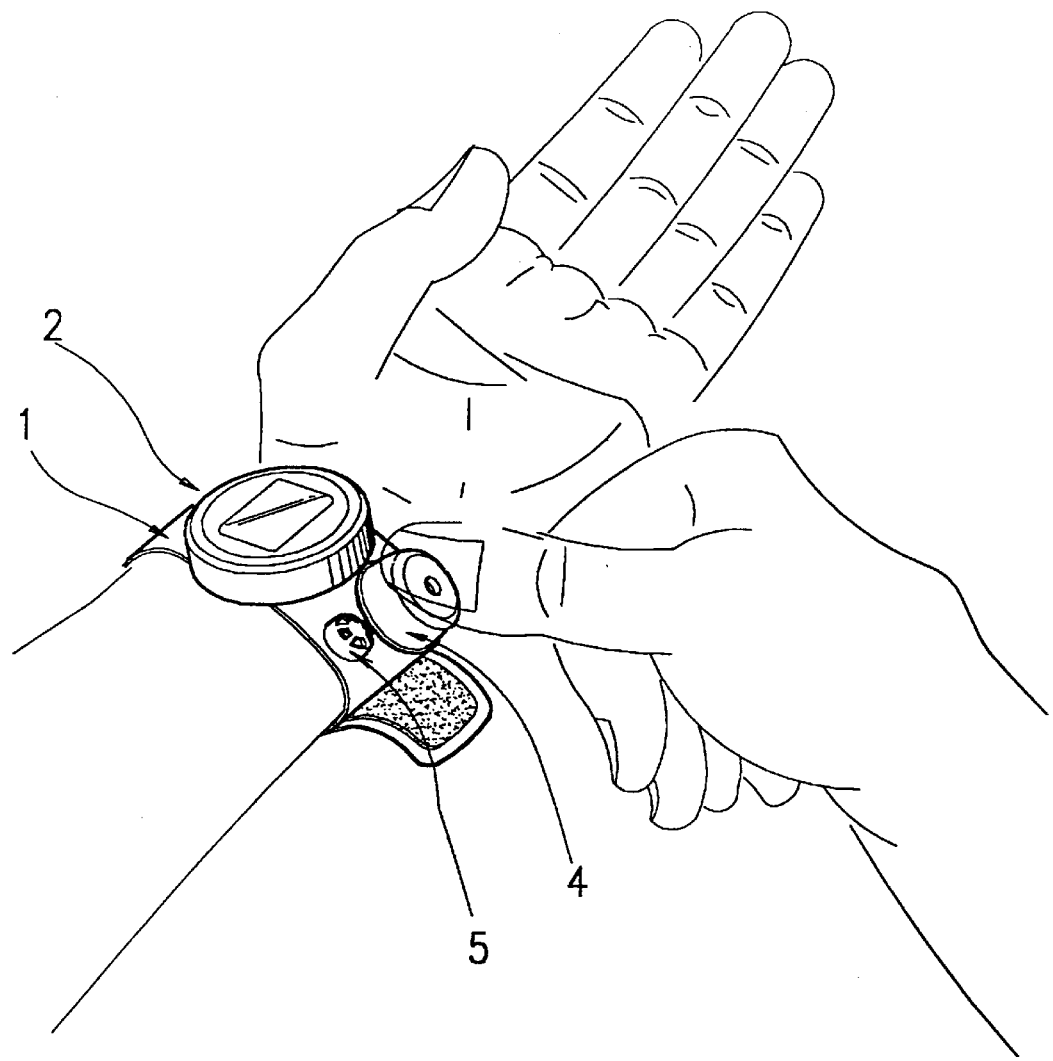
FIG. 3 is an applied view of the present invention, showing the wrist band type electronic sphygmomanometer fastened to the wrist and operated.

Referring to FIGS. 2 and 3, by means of the hook and loop materials 6, the wrist band 1 can be mounted on the wrist and secured thereto at the desired tightness. A pressure sensor 7 is disposed at the bottom side of the electronic manometer and timepiece assembly 2, and adapted to detect the pressure of the blood in an artery. Detected analog signal from the pressure sensor 7 is converted into corresponding electric signal by an electronic converter (not shown) for display through a display unit of the electronic manometer and timepiece assembly 2. The electronic converter is of the known art and not within the scope of the invention, therefore it is not described herein in detail. The rubber-bulb 4 comprises an one-way air valve on the inside, which permits air to be driven into the inflatable chamber 3 when the rubber-bulb 4 is operated, and prohibits a reverse flow of air.

The relief valve 5 permits air to be released from the inflatable chamber 3. After the wrist band I has been fastened to the wrist and the inflatable chamber 3 has been inflated, the relief valve 5 is opened to let air get out of the inflatable chamber 3, and the pressure change is detected by the pressure sensor 7, causing the display to indicate the pressure of the blood and the strength of the pulse beat by digital. The electronic manometer and timepiece assembly 2 is a combination of a blood pressure manometer and an electronic watch. Therefore, the electronic sphygmomanometer is used as a wrist-watch when it is not used for measuring the pressure of the blood.

What the invention claimed is:

1. A wrist band type electronic sphygmomanometer comprising an inflatable wrist band, hook and loop materials provided at two opposite ends of said inflatable wrist band for securing said inflatable wrist band to the user's wrist, a rubber-bulb provided at said inflatable wrist band and operated to inflate said inflatable wrist band, a relief valve provided at said inflatable wrist band and controlled to release air from said inflatable wrist band, and an electronic manometer and timepiece assembly provided at said wrist band to indicate time and to measure and indicate the user's blood pressure and strength of pulse beat through a pressure sensor thereof.

* * * * *